United States Patent [19]
Neeser

[11] Patent Number: 5,957,126
[45] Date of Patent: Sep. 28, 1999

[54] NASAL DILATOR WITH FIBROUS PSA

[75] Inventor: Roger Dwayne Neeser, St. Paul, Minn.

[73] Assignee: 3M Innovative Properties Company, St. Paul, Minn.

[21] Appl. No.: 08/982,239

[22] Filed: Dec. 1, 1997

[51] Int. Cl.[6] .......................... A61M 29/00; A61M 16/00; A61M 37/00; A61F 13/00
[52] U.S. Cl. .............................. 128/200.24; 606/204.45; 606/199
[58] Field of Search ................... 128/200.24, 207.18; 606/204.45, 199

[56] References Cited

U.S. PATENT DOCUMENTS

| | | | |
|---|---|---|---|
| 1,292,083 | 1/1919 | Sawyer | 606/204.45 |
| 4,302,500 | 11/1981 | Flora | 428/284 |
| 4,919,999 | 4/1990 | Maria Van Soom | 428/284 |
| 5,032,450 | 7/1991 | Rechlicz et al. | 428/196 |
| 5,423,783 | 6/1995 | Battles et al. | 604/344 |
| 5,476,091 | 12/1995 | Johnson | 128/200.24 |
| 5,533,499 | 7/1996 | Johnson | 128/200.24 |
| 5,533,503 | 7/1996 | Doubek et al. | 128/200.24 |
| 5,549,103 | 8/1996 | Johnson | 128/200.24 |
| 5,560,974 | 10/1996 | Langley | 428/198 |
| 5,769,089 | 6/1998 | Hand et al. | 128/858 |

FOREIGN PATENT DOCUMENTS

| | | | |
|---|---|---|---|
| 23227/95 | 1/1997 | Australia | A61F 5/56 |
| 0 279 118 A2 | 8/1988 | European Pat. Off. | A61L 15/06 |
| 0 305 175 A1 | 8/1988 | European Pat. Off. | C08G 18/67 |
| 289561 | 10/1985 | Spain | A61F 5/56 |
| 94/23675 | 10/1994 | WIPO | A61F 5/56 |
| 97/38651 | 10/1997 | WIPO | A61F 5/56 |

*Primary Examiner*—Kimberly L. Asher
*Attorney, Agent, or Firm*—Gary L. Griswold; Robert W. Sprague; William J. Bond

[57] ABSTRACT

A nasal dilator comprising a backing substrate having a first face and a second face. On the first face, there is provided a fibrous pressure-sensitive adhesive layer that comprises an entangled web of pressure-sensitive adhesive fibers. The fibrous adhesive layer has a moisture vapor transmission rate (MVTR) of at least 1000 g/m$^2$/day, and an adhesion to skin of at least 20 g/2.5 cm. On the second face of the backing, there is provided a resilient spring which extends along the length of the backing and is attached to at least two end regions of the backing. The fibrous adhesive layer provides for a nasal dilator that can be repeatedly attached to a wearer's nose with minimal levels of skin damage or trauma upon removal and increased levels of comfort while being used.

32 Claims, 6 Drawing Sheets

NASAL DILATOR WITH FIBROUS PSA

BACKGROUND OF THE INVENTION

The invention relates to a pressure-sensitive adhesive nasal dilator, particularly nasal dilators which can be repeatedly adhered to the skin of a wearer with minimal skin trauma.

Nasal dilators are devices used to open up nasal passages to increase airflow through the nasal passage. Nasal dilators can be applied to the exterior surface of the nose. A biasing force from a spring element or the like exerts an outward force on the outer tissue wall opening of the nasal passages. These devices can be used for medical related problems such as a deviated septums, allergic swelling, or the like. These devices are also used to alleviate snoring, for increased athletic performance, and like uses. These devices are generally applied by a pressure-sensitive adhesive that attaches at least to the nasal skin of the tissue forming the outer side wall of the nasal passages. Examples of these nasal dilators are described in U.S. Pat. No. 5,549,103 and the references cited therein, including U.S. Pat. Nos. 4,414,977; 1,292,083; 1,950,839, and PCT 92/22340.

Users of these nasal dilators tend to use these devices repeatedly and they are applied and reapplied to the same patch of skin on either side of the nose. These repeated tapings can cause skin trauma or irritation, even when hypoallergenic pressure-sensitive adhesives are employed. The adhesive when worn for extended periods can cause the underlying skin to become overhydrated and even macerated which can result in excessive skin cells, or even skin layers, being stripped when the pressure-sensitive adhesive dilator device is removed. Even if the skin does not become overhydrated during use, repeated stripping of the dilators can cause skin trauma over time. Also, overhydration of the skin results in discomfort and loss of adhesion. There is a need for a nasal dilator that can be repeatedly applied with a pressure-sensitive adhesive with minimal levels of discomfort and low levels of skin trauma upon repeated removal of the dilator devices from the same skin area.

SUMMARY OF THE INVENTION

The invention is directed at a nasal dilator comprising a backing substrate having a first face and a second face. On the first face, there is provided a fibrous pressure-sensitive adhesive layer that comprises an entangled web of pressure-sensitive adhesive fibers. The fibrous adhesive layer has a moisture vapor transmission rate (MVTR) of at least 1000 g/m²/day, and an initial adhesion to skin of at least 20 g/2.5 cm. On the second face of the backing, there is provided a resilient spring which extends along the length of the backing and is attached to at least two end regions of the backing. The fibrous adhesive layer provides for a nasal dilator that can be repeatedly attached to a wearer's nose with minimal levels of skin damage or trauma upon removal and increased levels of comfort while being used.

DETAILED DESCRIPTION OF THE PREFERRED EMBODIMENTS

Figure 1:
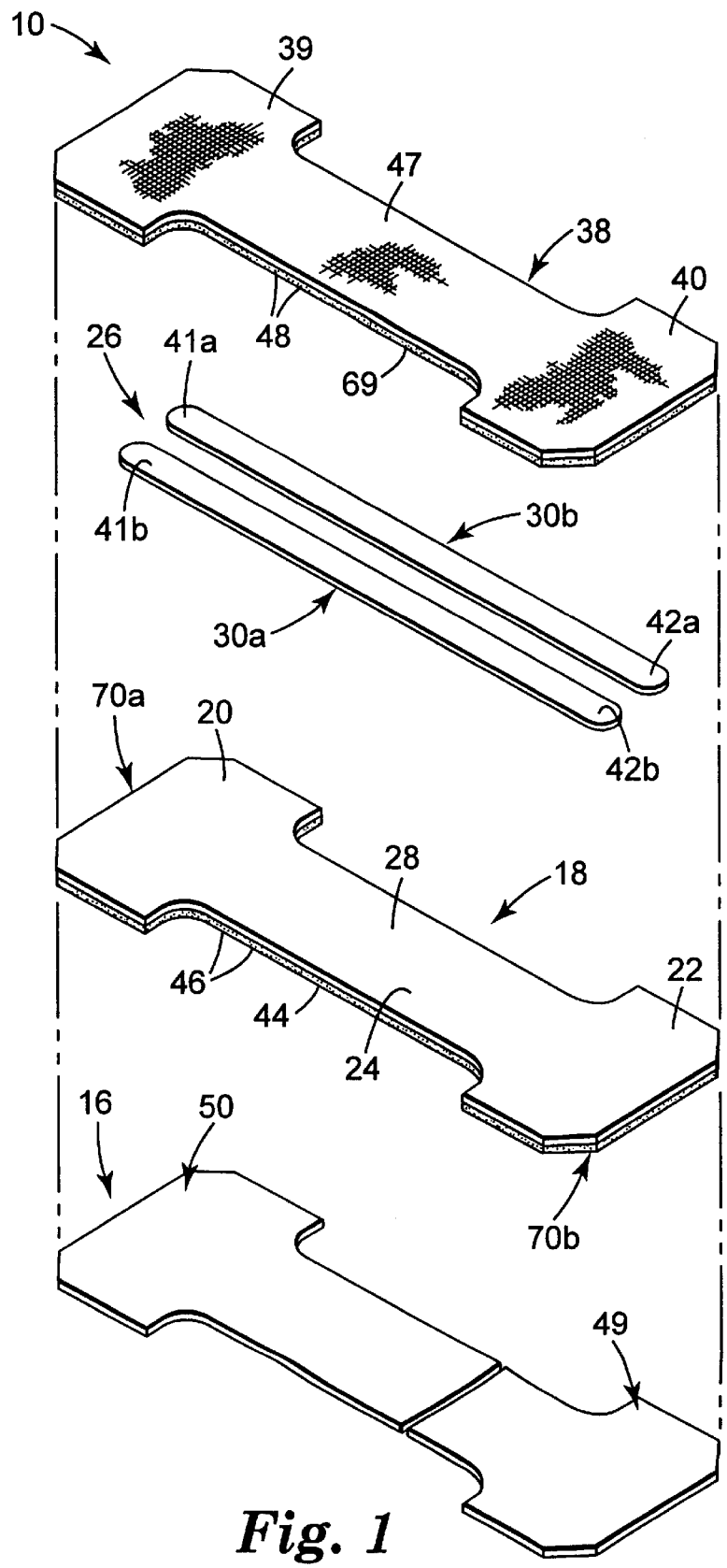
FIG. 1 is an exploded perspective view of a first embodiment of a nasal dilator in accordance with the present invention.
Figure 2:
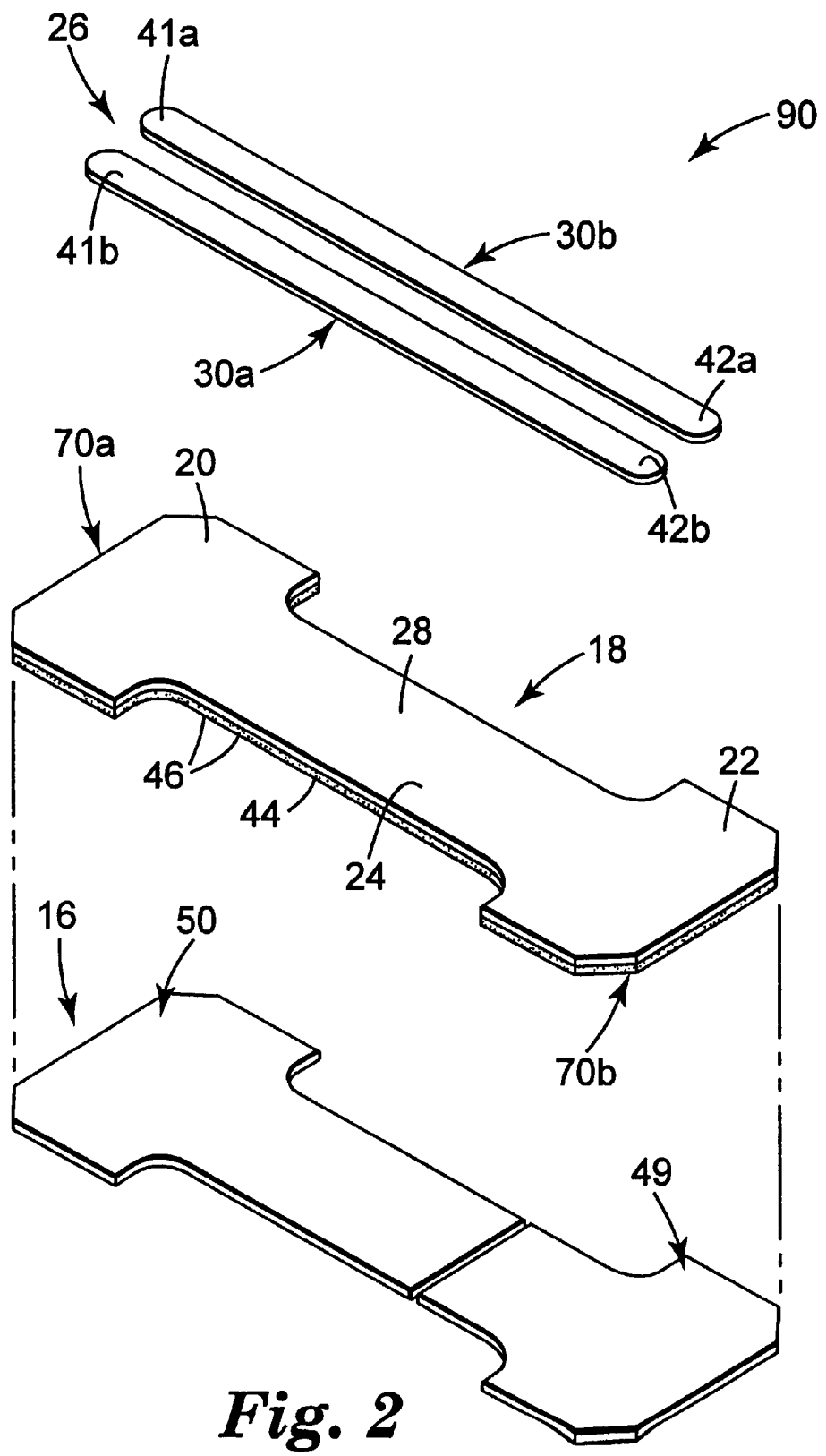
FIG. 2 is an exploded perspective view of a second embodiment of a nasal dilator in accordance with the present invention.
Figure 3:
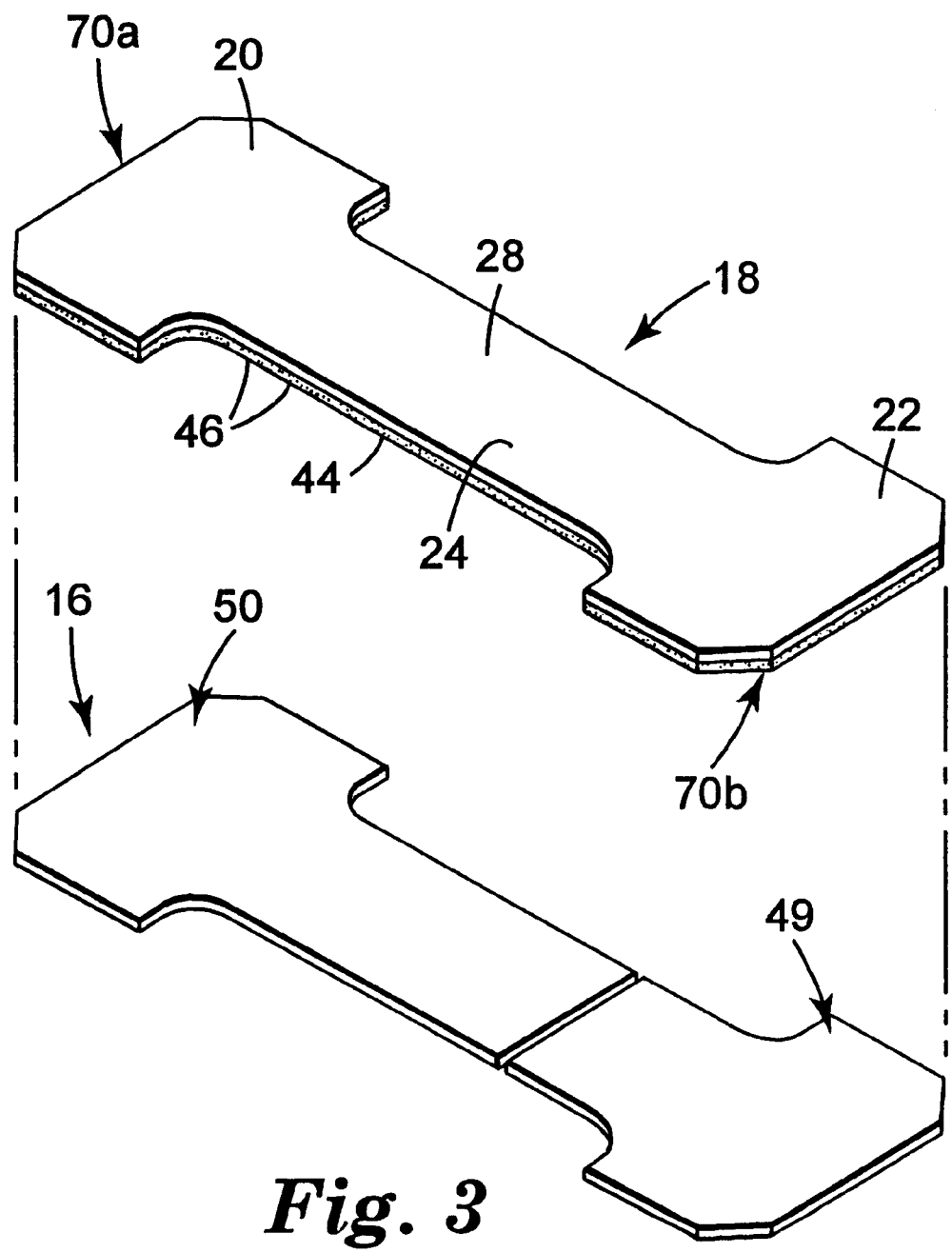
FIGS. 3 is an exploded perspective view of a third embodiment of a nasal dilator in accordance with the present invention.

The invention nasal dilator 10 is depicted generally in FIGS. 1, 2, and 3 are used in the manner described in U.S. Pat. No. 5,549,103, the substance of which is incorporated by reference in its entirety. The nasal dilator is applied as a pressure-sensitive adhesive article attached to the nose of the wearer at least at two end regions 20 and 22 of the backing 18. The invention adhesive layer 46 on at least these two ends 20 and 22 of a first face 44 is a low trauma fibrous pressure-sensitive adhesive layer 46 as will be described in more detail below. This adhesive layer provides significant improved performance by increases in the moisture vapor transmission rate (MVTR) and reducing skin trauma upon removal of the nasal dilators.

The nasal dilator includes a resistant spring 26 which preferably includes one and preferably two or more resilient spring elements 30a and 30b. These resilient spring elements operate similar to a leaf spring providing a recovery force when bent around the nose of from 5 to 50 grams, preferably 20 to 30 grams force. Each element 30a and 30b is a portion of the total recovery force. These resilient spring elements can be formed of any suitable resilient material including metal, thermoplastic films, consolidated nonwovens, resin impregnated nonwovens or the like. A preferred material is an oriented polyester film stay of a thickness of from 8 mils (200 microns) to 15 mils(375 microns), preferably about 13 mils ( 325 microns). This stay is generally from 2 to 4 mm wide and comes in various lengths depending on the intended wearer, generally from 40 to 80 mm. The resilient spring elements 30 have first end regions 41a and 41b and second end regions 42a and 42b which end regions extend into first end regions 20 and second end region 22, respectively. The resilient element end regions generally extend into at least 50 percent or more of the attached end regions 20 and 22 of the backing 18, preferably at least 75 percent or more. The resilient spring elements 30a and 30b preferably extend to within 500 microns or less of the first and second ends 70a and 70b of the backing 18.

The backing 18 preferably is a breathable material such as a nonwoven web, a perforated film or a microporous film. The intermediate segment 24 generally has a minimum width less than the maximum width of the two end regions 20 and 22. Generally, the backing is attached to the nose along its entire length. However, the two end regions 20 and 22 can be attached to the nose such as by adhesive bonding while intermediate section 24 is free of adhesive contact with the nose. The enlarged end regions 20 and 22 allow for more secure contact with the nose in the area where the maximum forces are exerted by the resilient spring 26, for better distribution of force exerted by the resilient spring 26 and increased overall wearer comfort.

The resilient spring elements 30a and 30b are generally attached to the backing 18 by adhesive but other means of attachment could also be used, such as thermal bonding, sonic welding, physical entrapment (tube), or the like. Generally, the resilient spring elements are attached to the backing 18 along their entire length. However, the resilient spring elements 30a and 30b can be attached only to the end regions 20 and 22 of the backing 18 such as by patterned adhesive bonding, or use of a masking element in the intermediate segment 24. As shown in FIG. 1, the dilator 10 also preferably includes a top facing layer 38 which can be a breathable material as backing layer 18, or other suitable thin conformable material such as a nonwoven web such as a spunbond or meltblown web, a thin thermoplastic film such as a porous or perforated polyethylene film, on a woven or knitted material. This top facing layer is attached to the backing layer by adhesive lamination or the like and could also be attached to the resilient spring elements 30a and 30b. A suitable method of attachment is by use of an adhesive layer 48 on a bottom surface 69, which could be a pressure-sensitive adhesive or a hot melt adhesive. The top facing layer generally has a first end region 39, a second end region 40, and an intermediate section 47 which may be mirror images of the backing layer first end region 20, second end region 22, and intermediate section 24, respectively. However, the top facing layer can be attached primarily to the resilient elements 30a and 30b and extend to a minor degree to cover the backing layer around the periphery of the resilient spring elements. The top facing layer is primarily used to keep the resilient member attached to the backing layer, for aesthetics and comfort and to provide a more structurally integral laminate.

The low trauma fibrous adhesive layer preferably is protected prior to use by one or more conventional release liners. There can be provided two release liners 49 and 50.

FIG. 2 shows an alternative embodiment of the invention where no top facing layer 38 is employed. In all other respects, the nasal dilator 90 of FIG. 2 is identical to the FIG. 1 embodiment.

FIG. 3 shows another alternative embodiment of the invention where backing 18 is also the resilient spring element. In this embodiment, the backing may be formed of any suitable material including metal, thermoplastic films, consolidated nonwovens, resin impregnated nonwovens or the like. Preferably, the material may be formed by profile extruding a thermoplastic polymer such as polyester, polyethylene, polypropylene, blends of polymers, copolymers, or the like. Backing 18 may be attached to the nose along the backings entire length or preferably only at ends 20 and 22 such as by patterned adhesive bonding, or use of a masking element over the adhesive in the intermediate segment 24.

Figure 4:
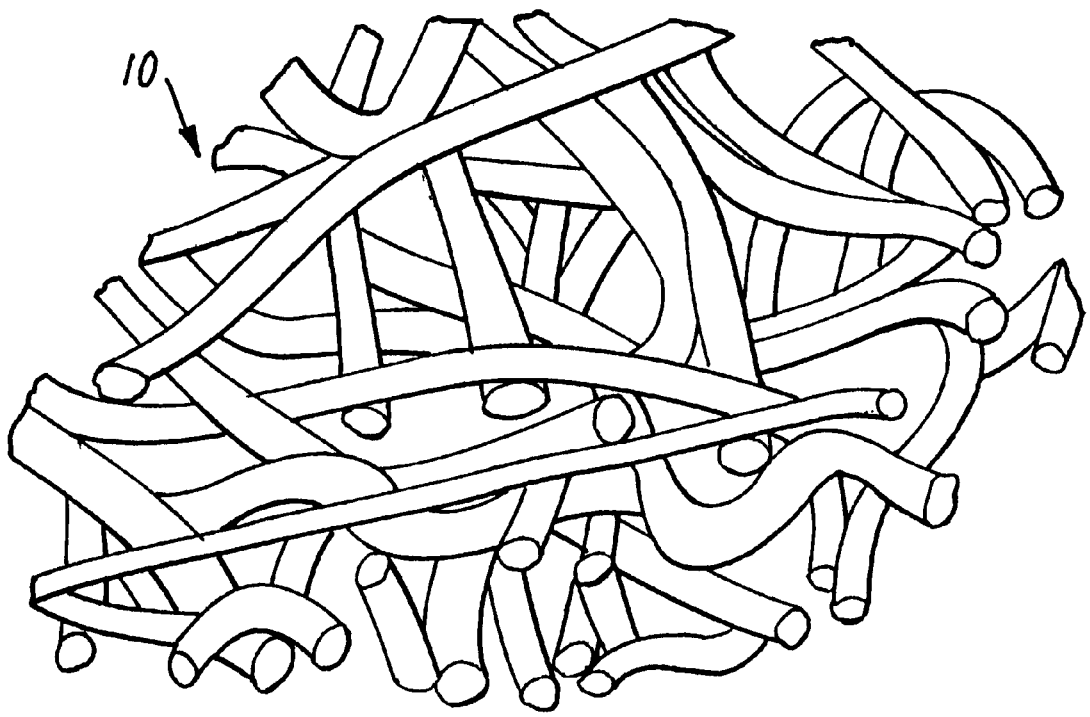
FIG. 4 is a perspective view of the breathable fibrous adhesive nonwoven web used in the invention nasal dilator.
Figure 5:
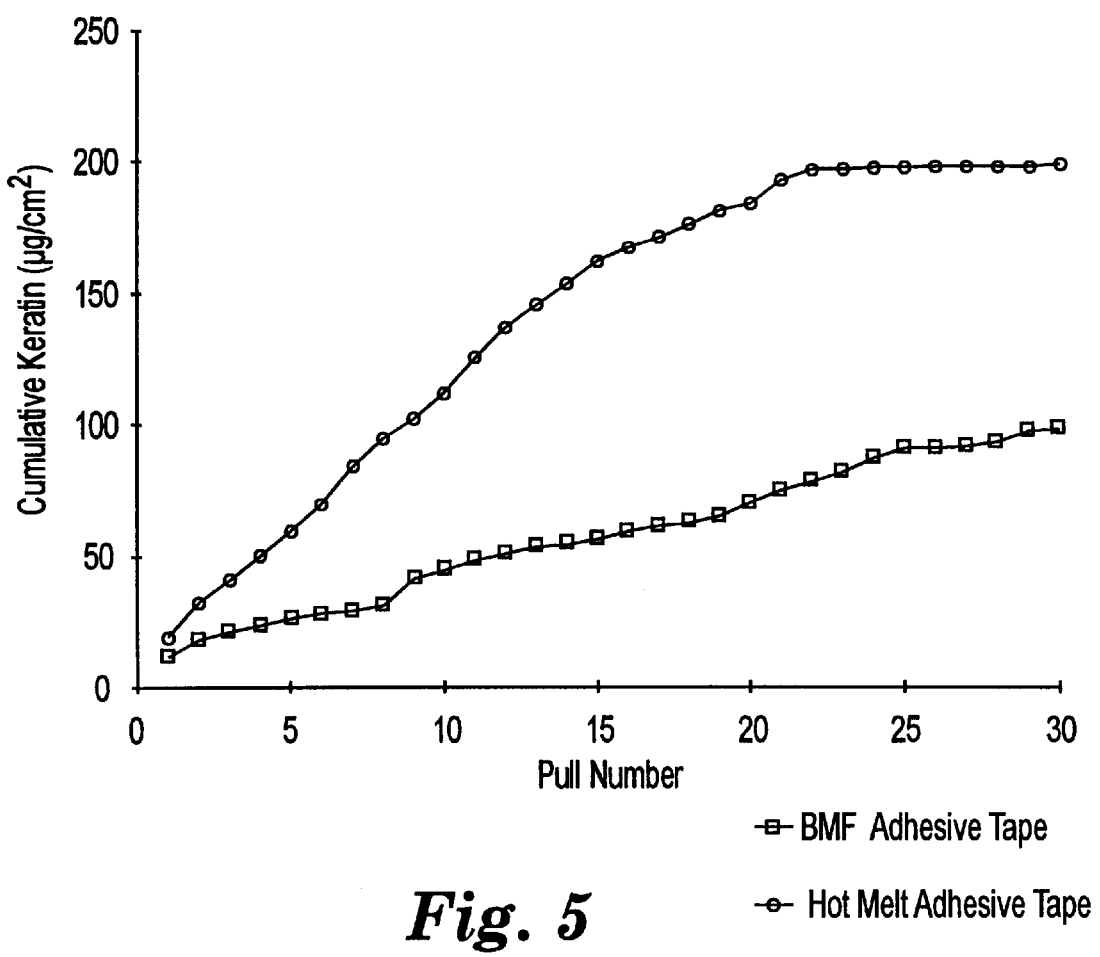
FIGS. 5 and 6 are graphs of cumulative keratin removal versus pulls of the invention tape from subjects.
Figure 6:
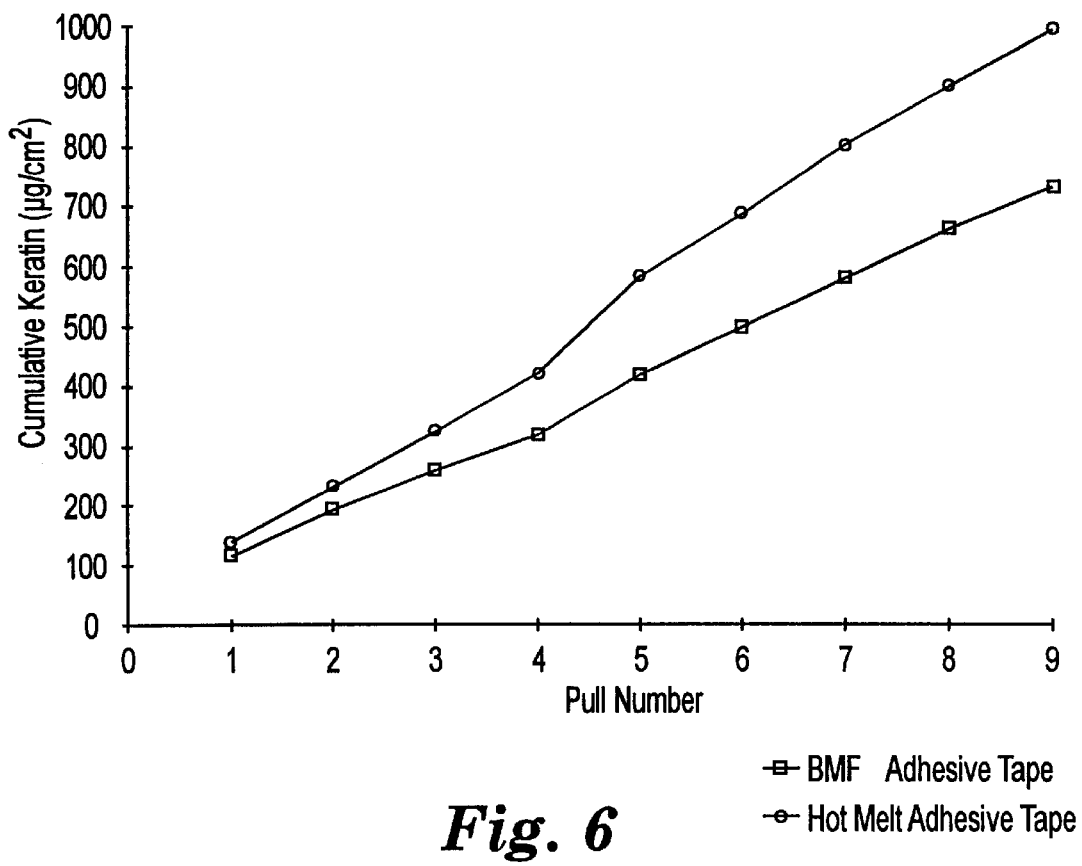

The low trauma fibrous pressure-sensitive adhesive layer is formed from coherent pressure-sensitive adhesive fibers which are intimately entangled each with the other in the form of a coherent breathable fibrous adhesive nonwoven web, attached to the backing 18. Suitable pressure-sensitive adhesive fiber webs 10, as shown in FIG. 4, can be formed as melt blown microfiber webs using the apparatus discussed, for example, in Wente, Van A., "Superfine Thermoplastic Fibers", *Industrial Engineering Chemistry*, Vol. 48, pages 1342–1346, Wente, Van A. et al., "Manufacture of Superfine Organic Fibers", Report No. 4364 of the Naval Research Laboratories, published May 25, 1954, and in U.S. Pat. Nos. 3,849,241; 3,825,379; and others. These microfine fibers are termed melt blown fibers and are generally substantially continuous and form into a coherent web between the exit die orifice and a collecting surface by entanglement of the microfibers due in part to the turbulent airstream in which the fibers are entrained. Further, suitable pressure-sensitive adhesive fibers used in the invention nasal dilator can be formed by other conventional melt spinning processes, such as spunbond processes where the fibers are collected in a web form immediately upon formation. Generally, the adhesive fibers are 100 microns or less in diameter when formed by melt spinning type processes, preferably 50 microns or less.

The invention nasal dilator preferably also comprises non-pressure-sensitive adhesive fibrous material intimately commingled with the pressure-sensitive adhesive fibers. The commingled pressure-sensitive adhesive fibers or microfibers and non-pressure-sensitive adhesive fibrous material can be present in separate individual fibers or the pressure-sensitive adhesive fibers or microfibers and the non-pressure-sensitive material can form distinct regions in a conjugate fiber and/or be part of a blend. For example, conjugate fibers can be in the form of two or more layered fibers, sheath-core fiber arrangements or in "island in the sea" type fiber structures. In this case, one component layer would comprise the pressure-sensitive adhesive fiber or microfiber and a second component layer would comprise the non-pressure-sensitive adhesive fibrous material. Generally with any form of multicomponent conjugate fibers, the pressure-sensitive adhesive fiber component will provide at least a portion of the exposed outer surface of the multicomponent conjugate fiber. Preferably, the individual components of the multicomponent conjugate fibers will be present substantially continuously along the fiber length in discrete zones, which zones preferably extend along the entire length of the fibers. The individual fibers generally are of a fiber diameter of less than 100 microns, preferably less than 50 microns or 25 microns for microfibers.

Conjugate fibers can be formed, for example, as a multilayer fiber as described, for example, in U.S. Pat. No. 5,238,733; 5,601,851; or PCT Publication WO 97/2375. Multilayered and sheath-core melt blown microfibers are described, for example, in U.S. Pat. No. 5,238,733, the substance of which is incorporated herein by reference in its entirety. This patent describes providing a multicomponent melt blown microfiber web by feeding two separate flow streams of polymer material into a separate splitter or combining manifold. The split or separated flow streams are generally combined immediately prior to the die or die orifice. The separate flow streams are preferably established into melt streams along closely parallel flow paths and combined where they are substantially parallel to each other and the flow path of the resultant combined multilayered flow stream. This multilayered flow stream is then fed into the die and/or die orifices and through the die orifices. Air slots are disposed on either side of a row of die orifices directing uniform heated air at high velocities at the extruded multicomponent melt streams. The hot high velocity air draws and attenuates the extruded polymeric material which solidifies after traveling a relatively short distance from the die. The high velocity air becomes turbulent between the die and the collector surface causing the melt blown fibers entrained in the airstream to mutually entangle and form a coherent nonwoven web. The either solidified or partially solidified fibers are then collected on a surface by known methods. Also, other fibers such as staple fibers and/or particulates can be fed into this turbulent airstream thereby getting incorporated into the forming coherent nonwoven web. This can be done, for example, by using a macrodropper, a second fiber forming die or other known methods.

Alternatively, conjugate fibers can be formed by a spunbond process such as described in U.S. Pat. No. 5,382,400 where separate polymer flow streams are fed via separate conduits to a spinneret for producing conjugate fibers of a conventional design. Generally, these spinnerets include a housing containing a spin pack with a stack of plates which form a pattern of openings arranged to create flow paths for directing the separate polymer components separately through the spinneret. The spinneret can be arranged to extrude the polymer vertically or horizontally in one or more rows of fibers.

An alternative arrangement for forming melt blown conjugate fibers is described for example, in U.S. Pat. No. 5,601,851. The polymer flow streams are separately fed to each individual die orifice by the use of grooves cut in a distributing and/or separating plate. This arrangement can be used to separately extrude different polymers from different individual orifices to provide separate distinct fibers which form a coherent entangled web having a substantially uniform distribution of the differing fibers. By feeding two, separate polymers to an individual die orifice a conjugate fiber can be formed. The apparatus described is suitably used in a melt blowing type arrangement where the die orifices are formed in a row along the die.

Commingled non-pressure-sensitive fibers can be discrete fibers such as staple fibers or continuous fibers such as melt blown or spun bond fibers. These fibers can significantly increase the moisture vapor transmission rate of the adhesive layer when present in relatively low amounts ranging from 2 to 20 percent. This increase in MVTR increases wearer comfort. Particularly, this relatively small amount of commingled fiber increased the lateral MVTR allowing moisture to exit the side edges of the adhesive such that even if the backing substrate is not breathable (e.g., due to adhesive lamination to the resilient spring 26 and/or a top facing layer 38) wearer comfort is increased due to lateral breathability.

The pressure-sensitive adhesive component comprises an extrudable pressure-sensitive adhesive suitable for melt blowing (generally this requires the adhesive to have an apparent viscosity of from 150 to 800 poise, measured by a capillary rheometer) or other fiber spinning processes such as spunbond processing. With conjugate fibers or conformed fibers of different polymers or blends formed from a single die or spinneret, the viscosities of the separate polymer flowstreams should be fairly closely matched for uniform fiber and web formation, but this is not required. Generally matching viscosities will ensure more uniformity in the conjugate fibers formed in terms of minimizing polymer mixing, which mixing can result in fiber breakage and formation of shot (small particulate polymer material), and lower web tensile properties. However, the presence of discontinuous fibers or shot is not necessarily undesirable as long as the fibrous adhesive layer has the desired overall adhesive strength.

The particular pressure-sensitive adhesive used in forming discrete pressure-sensitive adhesive fibers, conjugate fibers or blends (in either discrete or conjugate fibers) depends on the adhesive formulation in view of the desired adhesion level as taught in the invention examples and the non-pressure-sensitive adhesive material polymers selected in the case of polymer blends or conjugate fibers. The pressure-sensitive adhesive selected is generally any hot melt extrudable copolymer or composition having a viscosity in the melt phase suitable for fiber forming by melt processing. Suitable classes of pressure-sensitive adhesives include acrylate adhesives, polyalphaolefin adhesives, rubber resin adhesives or the like. Suitable rubber resin adhesives would include those formed using a tackified elastomer where a preferred elastomer is an A-B type block copolymer wherein the A blocks and B blocks are configured in linear (such as diblock or triblock copolymers), radial or star configurations. The A block is formed of a monoalkenylarene, preferably a polystyrene block having a molecular weight between 4000 and 50,000, preferably between 7000 and 30,000. The A block content is preferably about 10 to 50 weight percent, preferably about 10 to 30 weight percent of the block copolymer. Other suitable A blocks may be formed from alpha-methylstyrene, t-butyl-styrene and other ring alkylated styrenes, as well as mixtures thereof. The B block is formed of an elastomeric conjugated diene, generally polyisoprene, polybutadiene or copolymers thereof having an average molecular weight from about 5000 to about 500,000, preferably from about 50,000 to about 200,000. The B block dienes can also be hydrogenated. The B block content is generally 90 to 50 percent, preferably 90 to 70 percent by weight. The tackifying components for the elastomer based adhesives generally comprise solid tackifying resin and/or a liquid tackifier or plasticizer. Preferably, the tackifying resins are selected from the group of resins at least partially compatible with the polydiene B block portion of the elastomer. Although not preferred, generally a relatively minor amount of the tackifying resin can include resins compatible with the A block, which when present are generally termed end block reinforcing resins. Generally, end block resins are formed from aromatic monomer species. Suitable liquid tackifiers or plasticizers for use in the fastening tape tab adhesive composition include napthenic oils, paraffin oils, aromatic oils, mineral oils or low molecular weight rosin esters, polyterpenes and C-5 resins. Some suitable B-block compatible solid tackifying resins include C-5 resins, resin esters, polyterpenes and the like.

The tackifier portion of the pressure-sensitive adhesive generally comprises from 20 to 300 parts per 100 parts of the elastomer phase. Preferably, this is predominately solid tackifier, however, from 0 to 25 weight percent, preferably 0 to 10 weight percent of the adhesive composition can be liquid tackifier and/or plasticizer.

Suitable rubber resin adhesives for melt blown processing are discussed in EP 658351 which exemplifies melt-blown fibrous synthetic rubber resin type adhesives used in a disposable absorbent article to either immobilize particulate sorbents or used as a pressure-sensitive adhesive attachment (e.g., for a sanitary napkin). Suitable adhesives exemplified are styrene-isoprene-styrene triblock block copolymer based, where the copolymer has coupling efficiencies ranging from 42 to 65 percent (e.g., 58 to 35 percent polystyrene-polyisoprene diblock material would be present), tackified with C-5 hydrocarbon resins (WINGTACK PLUS and WINGTACK 10) and stabilized with antioxidants.

Generally, depending on the fiber formation process, suitable antioxidants and heat stabilizers could be used in the present invention to prevent the degradation of the adhesive during the fiber forming process or in use. Also, other conventional additives could be used such as UV absorbents, pigments, particulates, staple fibers or the like.

Suitable poly(acrylates) are derived from: (A) at least one monofunctional alkyl (meth)acrylate monomer (i.e., alkyl acrylate and alkyl methacrylate monomer); and (B) at least one monofunctional free-radically copolymerizable reinforcing monomer. The reinforcing monomer has a homopolymer glass transition temperature ($T_g$) higher than that of the alkyl (meth)acrylate monomer and is one that increases the glass transition temperature and modulus of the resultant copolymer. Monomers A and B are chosen such that a copolymer formed from them is extrudable and capable of forming fibers. Herein, "copolymer" refers to polymers containing two or more different monomers, including terpolymers, tetrapolymers, etc.

Preferably, the monomers used in preparing the pressure-sensitive adhesive copolymer fibers of the present invention include: (A) a monofunctional alkyl (meth)acrylate monomer that, when homopolymerized, generally has a glass transition temperature of no greater than about 0° C.; and (B)

a monofunctional free-radically copolymerizable reinforcing monomer that, when homopolymerized, generally has a glass transition temperature of at least about 10° C. The glass transition temperatures of the homopolymers of monomers A and B are typically accurate to within ±5° C. and are measured by differential scanning calorimetry.

Monomer A, which is a monofunctional alkyl acrylate or methacrylate (i.e., (meth)acrylic acid ester), contributes to the flexibility and tack of the copolymer. Preferably, monomer A has a homopolymer $T_g$ of no greater than about 0° C. Preferably, the alkyl group of the (meth)acrylate has an average of about 4 to about 20 carbon atoms, and more preferably, an average of about 4 to about 14 carbon atoms. The alkyl group can optionally contain oxygen atoms in the chain thereby forming ethers or alkoxy ethers, for example. Examples of monomer A include, but are not limited to, 2-methylbutyl acrylate, isooctyl acrylate, lauryl acrylate, 4methyl-2-pentyl acrylate, isoamyl acrylate, sec-butyl acrylate, n-butyl acrylate, n-hexyl acrylate, 2-ethylhexyl acrylate, n-octyl acrylate, n-decyl acrylate, isodecyl acrylate, isodecyl methacrylate, and isononyl acrylate. Other examples include, but are not limited to, poly-ethoxylated or -propoxylated methoxy (meth)acrylate (i.e., poly(ethylene/propylene oxide) mono-(meth)acrylate) macromers (i.e., macromolecular monomers), polymethylvinyl ether mono (meth)acrylate macromers, and ethoxylated or propoxylated nonyl-phenol acrylate macromers. The molecular weight of such macromers is typically about 100 grams/mole to about 600 grams/mole, and preferably, about 300 grams/mole to about 600 grams/mole. Combinations of various monofunctional monomers categorized as an A monomer can be used to make the copolymer used in making the fibers of the present invention.

Monomer B, which is a monofunctional free-radically copolymerizable reinforcing monomer; increases the glass transition temperature of the copolymer. As used herein, "reinforcing" monomers are those that increase the modulus of the adhesive, and thereby its strength. Preferably, monomer B has a homopolymer $T_g$ of at least about 10° C. More preferably, monomer B is a reinforcing monofunctional (meth)acrylic monomer, including an acrylic acid, a methacrylic acid, an acrylamide, and an acrylate. Examples of monomer B include, but are not limited to, acrylamides, such as acrylamide, methacrylamide, N-methyl acrylamide, N-ethyl acrylamide, N-methylol acrylamide, N-hydroxyethyl acrylamide, diacetone acrylamide, N,N-dimethyl acrylamide, N,N-diethyl acrylamide, N-ethyl-N-aminoethyl acrylamide, N-ethyl-N-hydroxyethyl acrylamide, N,N-dimethylol acrylamide, N,N-dihydroxyethyl acrylamide, t-butyl acrylamide, dimethylaminoethyl acrylamide, N-octyl acrylamide, and 1,1,3,3-tetramethylbutyl acrylamide. Other examples of monomer B include acrylic acid and methacrylic acid, itaconic acid, crotonic acid, maleic acid, fumaric acid, 2,2-(diethoxy)ethyl acrylate, hydroxyethyl acrylate or methacrylate, 2-hydroxypropyl acrylate or methacrylate, methyl methacrylate, isobutyl acrylate, n-butyl methacrylate, isobornyl acrylate, 2(phenoxy)ethyl acrylate or methacrylate, biphenylyl acrylate, t-butylphenyl acrylate, cyclohexyl acrylate, dimethyladamantyl acrylate, 2-naphthyl acrylate, phenyl acrylate, N-vinyl pyrrolidone, and N-vinyl caprolactam. Combinations of various reinforcing monofunctional monomers categorized as a B monomer can be used to make the copolymer used in making the fibers of the present invention.

The acrylate copolymer is preferably formulated to have a resultant $T_g$ of less than about 25° C. and more preferably, less than about 0° C. Such acrylate copolymers preferably include about 60 parts to about 98 parts per hundred of at least one alkyl (meth)acrylate monomer and about 2 parts to about 40 parts per hundred of at least one copolymerizable reinforcing monomer. Preferably, the acrylate copolymers have about 85 parts to about 98 parts per hundred or at least one alkyl (meth)acrylate monomer and about 2 parts to about 15 parts of at least one copolymerizable reinforcing monomer.

A crosslinking agent can be used if so desired to build the molecular weight and the strength of the copolymer, and hence improve the integrity and shape of the fibers. Preferably, the crosslinking agent is one that is copolymerized with monomers A and B. The crosslinking agent may produce chemical crosslinks (e.g., covalent bonds). Alternatively, it may produce physical crosslinks that result, for example, from the formation of reinforcing domains due to phase separation or acid base interactions. Suitable crosslinking agents are disclosed in U. S. Pat. Nos. 4,379,201 (Heilman), 4,737,559 (Kellen), 5,506,279 (Babu et al.), and 4,554,324 (Husman).

This crosslinking agent is preferably not activated towards crosslinking until after the copolymer is extruded and the fibers are formed. Thus, the crosslinking agent can be a photocrosslinking agent, which, upon exposure to ultraviolet radiation (e.g., radiation having a wavelength of about 250 nanometers to about 400 nanometers), causes the copolymer to crosslink. Preferably, however, the crosslinking agent provides crosslinking, typically, physical crosslinking, without further processing. Physical crosslinking can occur through phase separation of domains which produces thermally reversible crosslinks. Thus, acrylate copolymers prepared from a crosslinker that provides reversible physical crosslinking are particularly advantageous in the preparation of fibers using a melt process.

Preferably, the crosslinking agent is (1) an acrylic crosslinking monomer, or (2) a polymeric crosslinking material having a copolymerizable vinyl group. More preferably the crosslinking agent is a polymeric material having a copolymerizable vinyl group. Preferably, each of these monomers is a free-radically polymerizable crosslinking agent capable of copolymerizing with monomers A and B. Combinations of various crosslinking agents can be used to make the copolymer used in making the fibers of the present invention. It should be understood, however, that such crosslinking agents are optional.

The acrylic crosslinking monomer is preferably one that is copolymerized with monomers A and B and generates free radicals in the polymer backbone upon irradiation of the polymer. An examples such a monomer is an acrylated benzophenone as described in U.S. Pat. No. 4,737,559 (Kellen et al.).

The polymeric crosslinking materials that have a copolymerizable vinyl group is preferably represented by the general formula X—(Y)$_n$—Z wherein: X is a copolymerizable vinyl group; Y is a divalent linking group where n can be zero or one; and Z is a monovalent polymeric moiety having a $T_g$ greater than about 20° C. and a weight average molecular weight in the range of about 2,000 to about 30,000 and being essentially unreactive under copolymerization conditions. Particularly preferred vinyl-terminated polymeric monomers useful in making the mnicrofibers of the present invention are further defined as having: an X group which has the formula HR$^1$C=CR$^2$—wherein R$^1$ is a hydrogen atom or a COOH group and R$^2$ is a hydrogen atom or a methyl group; a Z group which has the formula —{C(R$^3$)

($R^4$)—$CH_2\}_n$—$R^5$ wherein $R^3$ is a hydrogen atom or a lower (i.e., $C_1$–$C_4$) alkyl group, $R^5$ is a lower alkyl group, n is an integer from 20 to 500, and $R^4$ is a monovalent radical selected from the group consisting of —$C_6H_4R^6$ and —$CO_2R^7$ wherein $R^6$ is a hydrogen atom or a lower alkyl group and $R^7$ is a lower alkyl group.

Such vinyl-terminated polymeric crosslinking monomers are sometimes referred to as macromolecular monomers (i.e., "macromers"). Once polymerized with the (meth) acrylate monomer and the reinforcing monomer, a vinyl-terminated polymeric monomer of this type forms a copolymer having pendant polymeric moieties which tend to reinforce the otherwise soft acrylate backbone, providing a substantial increase in the shear strength of the resultant copolymer adhesive. Specific examples of such crosslinking polymeric materials are disclosed in U.S. Pat. No. 4,554,324 (Husman et al.).

If used, the crosslinking agent is used in a curatively effective amount, by which is meant an amount that is sufficient to cause crosslinking of the pressure-sensitive adhesive to provide the desired final adhesion properties to the substrate of interest. Preferably, if used, the crosslinking agent is used in an amount of about 0. 1 part to about 10 parts, based on the total amount of monomers.

If a photocrosslinking agent has been used, the adhesive in the form of fibers can be exposed to ultraviolet radiation having a wavelength of about 250 nm to about 400 nm. The radiant energy in this preferred range of wavelength required to crosslink the adhesive is about 100 milliJoules/centimeter$^2$ (mJ/cm$^2$) to about 1,500 mJ/cm$^2$, and more preferably, about 200 mJ/cm$^2$ to about 800 mJ/cm$^2$.

The acrylate pressure-sensitive adhesives of the present invention can be synthesized by a variety of free-radical polymerization processes, including solution, radiation, bulk, dispersion, emulsion, and suspension polymerization processes. Bulk polymerization methods, such as the continuous free radical polymerization method described in U.S. Pat. Nos. 4,619,979 or 4,843,134 (both to Kotnour et al.), the essentially adiabatic polymerization methods using a batch reactor described in U.S. Pat. No. 5,637,646 (Ellis), and the methods described for polymerizing packaged pre-adhesive compositions described in International Patent Application No. WO 96/07522, may also be utilized to prepare the polymer used in the preparation of the fibers of the present invention.

The acrylate pressure-sensitive adhesive compositions of the present invention can include conventional additives such as tackifiers (wood rosin, polyesters, etc.), plasticizers, flow modifiers, neutralizing agents, stabilizers, antioxidants, fillers, colorants, and the like, as long as they do not interfere in the fiber-forming melt process. Initiators that are not copolymerizable with the monomers used to prepare the acrylate copolymer can also be used to enhance the rate of polymerization and/or crosslinking. These additives are incorporated in amounts that do not materially adversely affect the desired properties of the pressure-sensitive adhesives or their fiber-forming properties. Typically, they can be mixed into these systems in amounts of about 0.05 weight percent to about 25 weight percent, based on the total weight of the composition.

Suitable polyolefin adhesives would include tackified polyolefin elastomer type adhesives, or amorphous polyalphaolefin polymers suitable for forming hot melt pressure-sensitive adhesives with or without added tackifier. Such amorphous polyalphaolefins are generally copolymers of a $C_3$ to $C_5$ linear alpha-olefin(s) and a higher alpha-olefin(s) (generally $C_6$ to $C_{10}$ ). Preferred are copolymers of polyolefins with polyhexene, polyheptene, polyoctene, polynonene and/or polydecene. Such amorphous polyalphaolefins are described in U.S. Pat. Nos. 4,264,576; 3,954,697 and 4,072,812 where the amorphous polyalphaolefin copolymers can be used without added tackifiers to directly form a pressure-sensitive adhesive. These amorphous copolymers generally have from 40 to 60 mole percent of the higher alphaolefin comonomer(s). However, suitable compatible tackifying resins and plasticizing oils can be used which generally correspond to those used to tackify the synthetic AB block copolymer elastomers described above. For example, suitable compatible liquid or solid tackifiers would include hydrocarbon resins, such as polyterpenes, C-5 hydrocarbon resins, or polyisoprenes, also resin esters of aromatic or aliphatic acids would be suitable. If these tackifiers are used in sufficient amounts, the higher alpha olefin content can be as low as 15 mole percent and still suitable pressure-sensitive adhesives can be formed.

Suitable non-adhesive materials for use in forming conjugate fibers, for use in blends with the pressure-sensitive adhesive or for use as separate fibers, include polyolefins, polyesters, polyalkylenes, polyamides, polystyrenes, polyarylsulfones, polydienes or polyurethanes; these materials are preferably extensible or slightly elastomeric, but could be elastomeric. Preferred are extensible or slightly elastomeric polyolefins such as polyethylenes, polypropylenes, ethylene-propylene copolymers, ethylene/vinyl acetate copolymers, or metallocene-type polyethylenes having a density of greater than 0.87 grams/cm$^3$. Suitable elastomeric materials would include metallocene-type polyethylene copolymers (apparent density less than 0.87 grams/cm$^3$); polyurethanes (e.g., "MORTHANE"); polyolefin elastomers (e.g., ethylene/propylene/diene elastomers); A-B block copolymers, as described above, having A blocks formed of poly (vinyl arenes) such as polystyrene and B blocks formed of conjugated dienes such as isoprene, butadiene, or hydrogenated versions thereof (e.g., "KRATON" elastomers available from Shell Chemical Co.); polyetheresters (such as "ARNITAL", available from Akzo Plastics Co.); or polyamides (such as "PEBAX", available from Autochem Co.). Blends of elastomers, blends of nonelastomers or blends of both elastomers and nonelastomers can also be used for the non-pressure-sensitive adhesive fibers, conjugate fibers or in suitable blend fibers.

The non-pressure-sensitive adhesive material in fibrous form generally comprises 0 to 50 percent of the basis weight of the fibers in the fibrous adhesive web, preferably 2 to 20 percent, and preferably as discrete commingled fibers or in conjugate fibers. The non-pressure-sensitive fibrous material if present solely in the form of a blend with the pressure-sensitive adhesive material is preferably from 0 to 40 percent of the basis weight of the fibers forming the low trauma adhesive coated substrate, preferably of the substantially continuous fibers forming the fibrous adhesive layer. The use of the non-pressure-sensitive adhesive material with the pressure-sensitive adhesive material decreases adhesion, however, also advantagously increases breathability. Where the non-pressure-sensitive adhesive fibrous material is present as a discrete fiber, these fibers are generally intimately commingled with the pressure-sensitive adhesive fibers. If the non-pressure-sensitive fibrous component is present as commingled fibers, these fibers can be formed from the same die as per U.S. Pat. No. 5,601,851 above, or in a separate die which could direct the non-pressure-sensitive adhesive fibers directly, or subsequently, into the fiber stream containing the pressure-sensitive adhesive fibers prior to collection of either fiber on a collection surface. The use of multiple dies for forming commingled fibers is known in the art. Further, commingled fibers could be added as staple fibers as known in the art. The adhesive layer generally has a basis weight of from 5 to 200 $g/m^2$, preferably 20 to 100 $g/m^2$, wherein at least 50 percent of the adhesive layer is in the form of pressure-sensitive adhesive fibers, preferably 85 to 100 percent.

The nasal dilator of the invention generally can be applied to a skin surface and exhibit an initial adhesion of from 20 to 100 g/2.5 cm, preferably 30 to 70 g/2.5 cm, and can be removed from the skin of a user without significant increases in Trans Epidermal Water Loss (TEWL, as defined in the examples). Generally, the overall TEWL after 20 tape pulls (as defined in the examples) is less than 20 $g/m^2$/hour, 0. 5 hours after the last pull, where the original TEWL is generally from 3 to 7 $g/m^2$/hour. The cumulative amount of keratin removed from an area of skin after 20 pulls (as defined in the examples) from an average subject is generally less than with a comparable tape having a continuous hot-melt coated adhesive layer, preferably 20 percent less, and most preferably, 50 percent less on average. The moisture vapor transmission rate (MVTR) (as defined in the Examples) of the adhesive layer after one day is generally greater than 1000 $g/m^2$/day, preferably at least 3000 $g/m^2$/day, most preferably at least 10,000 $g/m^2$/day.

EXAMPLES

The following examples are offered to aid in understanding of the present invention and are not to be construed as limiting the scope thereof. Unless otherwise indicated, all parts and percentages are by weight.

Test Protocols
Measurement of Transepidermal Water Loss (TEWL)

Evaporative water loss measurements provide an instrumental assessment of skin barrier function and skin trauma. The rate of water coming off of the skin, commonly termed Transepidermal Water Loss (TEWL), was measured with a ServoMed EP 2 Evaporimeter (Servo Med AB, Kinna, Sweden). The Evaporimeter consisted of a hand-held probe which was attached by a cable to a portable electronic display unit. At the end of the probe was an open cylinder that was 15.5 mm long and had a mean diameter of 12.5 mm. Two sensors within this open cylinder measured the temperature and relative humidity at two fixed points, approximately 4 mm apart, along the axis normal to the skin surface. This arrangement allowed the instrument to calculate an evaporative water loss, expressed in $g/m^2$/hr. The Evaporimeter was used in a test environment with a relative humidity of 35–45% and a temperature of 18–20° C. The test subject was present in such an environment for at least 15 minutes prior to measurement so that the skin reached an equilibrated state. Common TEWL values of undamaged skin are in the range of 3 to 7 $g/m^2$/hr, whereas values that range from 10 to 60 $g/m^2$/hr are indicative of damage to the epidermal skin barrier.

Keratin Assay Method

The keratin assay method was modified from that described by R. T. Tregear and P. Dirnhuber, "The Mass of Keratin Removed from the Stratum Corneum by Stripping with Adhesive Tape", *J. Investigative Dermatology*, 38: 375–381 (1961). Briefly, the method involved binding a stain in acid solution to keratin (protein) within the mass of tissue removed from the skin. Following acid washings to remove excess dye, bound dye was released from the protein with a basic solution, and the amount of dye present, determined by a spectrophotometer, was directly related to the amount of protein in the tissue. The concentration of dye in solution was compared to a standard concentration vs absorbence curve developed from a human keratin solution purchased from Sigma Chemical Company, St. Louis, Mo.

Standard Keratin Concentration Curve Preparation

One ml of water and either 0 µl, 5 µl, 10 µl, 20 µl, 40 µl, 80 µl, or 150 µl of a human keratin extract solution (Sigma, 7.7 mg/ml keratin) was placed into individual Centr/Por® (Spectrum Company, Laguna Hills, Calif.) centrifuge concentrators. One ml of dye solution (0.5 g Chromotrope FB per liter of 0.0 1N $H_2SO_4$) was then added to the keratin solution. The keratin/dye solution was allowed to stand overnight at room temperature. The tubes were then centrifuged at 2,000×g for one hour, after which the remaining solution was decanted off. One ml of 0.01N $H_2SO_4$ was then added to each tube and shaken vigorously. The tubes were recentrifuged for 15 minutes, solution decanted off, and the washing step repeated four more times. Following the last wash step 3 ml of 0.25N NaOH was added to each tube. The solutions were allowed to sit overnight, after which they were decanted into semi-micro cuvets and the dye concentrations determined with a spectrophotometer at a wave length of 508 nm.

Determination of Keratin on Adhesive Tapes

Two samples of known area were cut from each tape to be analyzed. The samples were placed into separate 5-ml plastic tubes. An aliquot (4.5 ml) of the dye solution was then added to each tube and the tubes allowed to sit overnight at room temperature. Each sample was washed five times with the acid solution and then an aliquot (4.5 ml) of the basic solution was added. The samples were again allowed to sit overnight at room temperature. Following the overnight extraction, all dye was removed from the tape samples and the amount of dye present was determined with the spectrophotometer as before. In calculating the concentration of keratin, the mean OD reading of control tape (unused tape sample) was first subtracted from the test sample value and any resulting negative OD values were set at zero. Samples values were reported as µg keratin per $cm^2$ of tape.

Adhesive Starting Materials
Adhesive 1 (Blown Micro Fiber (BMF)-Acrylate-PSA Web)

An acrylate-based BMF-PSA web was prepared using a melt blowing process similar to that described, for example, in Wente, Van A., "Superfine Thermoplastic Fibers," in *Industrial Engineering Chemistry*, Vol. 48, pages 1342 et seq (1956) or in Report No. 4364 of the Naval Research Laboratories, published May 25, 1954, entitled "Manufacture of Superfine Organic Fibers" by Wente, Van A.; Boone, C.D.; and Fluharty, E.L., except that the BMF apparatus utilized a single extruder which fed its extrudate to a gear pump that controlled the polymer melt flow. The gear pump fed a feedblock assembly that was connected to a melt-blowing die having circular smooth surface orifices (10/cm) with a 5:1 length to diameter ratio. The primary air was maintained at 220° C. and 241 KPa with a 0.076 cm gap width to produce a uniform web. The feedblock assembly was fed by a polymer melt stream (240° C.) comprised of isooctyl acrylate/acrylic acid/styrene macromer (IOA/AA/Sty, 92/4/4 ratio, Inherent Viscosity ~0.65 as measured by conventional means using a Cannon-Fenski #50 viscometer in a water bath controlled at 25° C. to measure the flow time of 10 ml of a polymer solution (0.2 g per deciliter polymer in ethyl acetate)) PSA, prepared as described in Example 2 of U.S. Pat. No. 5,648,166, which is incorporated herein by reference. Both the die and feedblock assembly were maintained at 220° C., and the die was operated at a rate of 178 g/hr/cm die width. The BMF-PSA web was collected on a double coated silicone release paper (Daubert Coated Products, Westchester, Ill.) which passed around a rotating drum collector at a collector to die distance of 17.8 cm. The resulting BMF-PSA web, comprising PSA microfibers having an average diameter of less than about 10–15 microns (as determined using a scanning electron microscope), had a basis weight of about 50 g/m$^2$.

Adhesive 2 (BMF-KRATON™-PSA Web)

A tackified KRATON™-based BMF-PSA web was prepared using a melt blowing process similar to that described for making Adhesive 1, except that a precompounded mixture of KRATON™1112 (100 parts, a styrene/isoprene/styrene block copolymer available from Shell Chemical, Houston, Tex.), ESCOREZ 1310LC (80 parts, an aliphatic hydrocarbon tackifier available from Exxon Chemical Co., Houston, Tex.) and ZONAREZ-A25 (10 parts, an alpha pinene type resin available from Arizona Chemical, Panama City, Fla.) was substituted for the IOA/AA/Sty PSA and delivered to one of the gear pumps at 190° C. The resulting BMF-PSA web had a basis weight of about 50 g/m$^2$.

Adhesive 3 (Hot-Melt Acrylate PSA Film)

The IOA/AA/Sty PSA starting material used to make Adhesive 1 was hot-melt extruded at 175° C. using a Hakke single screw extruder into a continuous film and collected between double coated silicone release liner. The resulting film had a basis weight of about 50 g/m$^2$.

Adhesive 4 (Hot-Melt KRATON™-PSA Film)

The KRATON™-PSA starting material used to make Adhesive 2 was hot-melt extruded at 160° C. using a Hakke single screw extruder into a continuous film and collected between double coated silicone release liner. The resulting film had a basis weight of about 50 g/m$^2$.

Example 1

BMF-Acrylate-PSA Tape (Polyurethane Backing)

The BMF-Acrylate-PSA web (Adhesive 1) was laminated to a melt blown polyurethane web (basis weight 100 g/m$^2$; prepared as described in Example 1 of U.S. Pat. No. 5,230,701, which is incorporated herein by reference) using a laboratory laminator having two rubber rollers with the bottom roller temperature set at 154° C. and the top roller temperature initially at room temperature. The resulting BMF-Acrylate-PSA tape was cut into 2.5 cm×7.6 cm samples which were later used in skin trauma evaluations.

Example 2

BMF-Acrylate-PSA Tape (Rayon Backing)

The BMF-Acrylate-PSA web (Adhesive 1) was laminated to nonwoven viscose-rayon web (prepared as described in Example 1 of U.S. Pat. No. 3,121,021, which is incorporated herein by reference) as described in Example 1. The resulting BMF-Acrylate-PSA tape was cut into 2.5 cm×7.6 cm samples which were later used in skin trauma evaluations.

Example 3

BMF-KRATON™-PSA Tape (Rayon Backing)

The BMF-KRATON™-PSA web (Adhesive 2) was laminated to a nonwoven viscose-rayon web as described in Example 1. The resulting BMF-KRATON™-PSA tape was cut into 2.5 cm×7.6 cm samples which were later used in skin trauma evaluations.

Comparative Example 1

Hot-Melt Acrylate-PSA Tape (Polyurethane Backing)

The continuous hot melt Acrylate-PSA film (Adhesive 3) was laminated to a melt blown polyurethane web as described in Example 1. The resulting hot-melt Acrylic-PSA tape was cut into 2.5 cm×7.6 cm samples which were later used in skin trauma evaluations.

Comparative Example 2

Hot-Melt Acrylate-PSA Tape (Rayon Backing)

The continuous hot melt Acrylate-PSA film (Adhesive 3) was laminated to a nonwoven viscose-rayon web as described in Example 1. The resulting hot-melt Acrylic-PSA tape was cut into 2.5 cm×7.6 cm samples which were later used in skin trauma evaluations.

Comparative Example 3

Hot-Melt KRATON™ PSA Tape (Rayon Backing)

The continuous hot melt KRATON™-PSA film from Example 4 was laminated to a nonwoven viscose-rayon web as described in Example 1. The resulting hot-melt KRATON™-PSA tape was cut into 2.5 cm×7.6 cm samples which were later used in skin trauma evaluations as described in Example 14.

SKIN TRAUMA EVALUATIONS

TEWL Measurements (Evaluation A)

A total of thirty tape samples of both the BMF-Acrylate-PSA tape with polyurethane backing (from Example 1) and the hot-melt Acrylate-PSA tape with polyurethane backing (from Comparative Example 1) were applied to a subject's bare-skin back over a three-day period. On day 1, ten hot-melt PSA tape samples were sequentially applied to Test Site A, each rolled down with a 2.3-kg roller four times (two cycles), and each removed immediately. Similarly, ten BMF-PSA tape samples were applied, rolled, and removed from Test Site B. The application of tape samples was then repeated on day two and day three. Test Site C was a control to which no tape samples were applied. After each of the ten tape pulls on each of the three days, TEWL was determined with a Servo Med Evaporimeter as described in the Test Protocols. A summary of results is provided in Table A.

TABLE A

| | TEWL (g/m$^2$/hr) | | | |
|---|---|---|---|---|
| Test Site (Tape Sample) | Day 1 (6 hr after 10th tape pull) | Day 2 (0.5 hr after 20th tape pull) | Day 3 (Just prior to tape application) | Day 3 (0.5 hr after 30th tape pull) |
| A (Hot-Melt PSA) (Comparative Example 1) | 13 | 70 | 45 | 83 |
| B (BMF-PSA) (Example 1) | 7 | 9 | 10 | 15 |
| C (Control - No Tape Applied) | 6 | 7 | 6 | 8 |

These results clearly show that the amount of skin trauma caused by the BMF-Acrylate-PSA tape samples was minimal and significantly lower than the trauma caused by the hot-melt Acrylate-PSA tape samples. After ten and twenty tape pulls the BMF-PSA tape results were comparable to the Control, and only after thirty tape pulls was there a small increase in TEWL values (up to 15 g/m$^2$/hr). In contrast, the hot-melt PSA tape results showed very large increases in TEWL values after just twenty tape pulls (up to 70 g/m$^2$/hr) and reached a value of 83 g/m$^2$/hr after thirty tape pulls. The results indicate that some skin healing apparently occurred overnight at the hot-melt PSA tape Site A (day-two value of 70 g/m$^2$/hr vs day-three value, before tape application, of 45 g/m$^2$/hr).

TEWL Measurements (Evaluation B)

Samples of both the BMF-KRATON™-PSA tape with Rayon backing (from Example 3) and the hot-melt KRATON™-PSA tape with Rayon backing (from Comparative Example 3) were applied to the bare-skin backs of two subjects (S1 and S2). In the case of Subject S1, 10 hot-melt PSA tape samples were sequentially applied to Test Site A, each rolled down with a 2.3-kg roller four times (two cycles), and each removed immediately. After four hours an 11th tape sample was similarly applied and allowed to remain in place overnight (about 18 hours). Immediately after removal of the overnight tape sample, two additional tape samples were then sequentially applied to the same Test Site and removed immediately. Similarly, a total of 13 BMF-PSA tape samples were applied, rolled, and removed from Test Site B. Test Site C was a control to which no tape samples were applied. In the case of Subject S2, the procedure was repeated exactly, except that four tape samples were applied on day two to give a total of 15 tape pulls. Initially before any tape sample was applied and four hours after the final tape pull at each Test Site, TEWL values were determined with a Servo Med Evaporimeter as described in the Test Protocols. A summary of results is provided in Table B.

TABLE B

| Test Site | TEWL (g/m$^2$/hr) | | | | | |
|---|---|---|---|---|---|---|
| | Subject S1 | | Subject S2 | | Average | |
| (Tape Sample) | Initial | Final | Initial | Final | Initial | Final |
| A (Hot-Melt PSA) (Comparative Example 3) | 3.57 | 36.99 | 3.57 | 29.08 | 3.57 | 33.04 |
| B (BMF-PSA) (Example 3) | 4.12 | 9.00 | 2.87 | 7.30 | 3.49 | 8.15 |
| C (Control - No Tape Applied) | 3.24 | 5.48 | 3.15 | 3.55 | 3.19 | 4.52 |

These results clearly show that the amount of skin trauma caused by the BMF-KRATON™-PSA tape samples was minimal and significantly lower than the trauma caused by the hot-melt KRATON™-PSA tape samples.

Keratin Removal Measurements (Evaluation C)

As part of Evaluation A described above, the cumulative keratin removed over three days (ten tape pulls/day) from Test Sites A and B was determined according to the Keratin Assay Method described in the Test Protocols. Evaluation results are shown graphically in FIG. 1. As is clearly evident from the data, a significantly greater amount of keratin was removed from Test Site A (hot-melt Acrylate-PSA Tape Site), thereby reflecting greater trauma, than was removed from Test Site B (BMF-Acrylate-PSA Tape Site).

Keratin Removal Measurements (Evaluation D)

Samples of both the BMF-Acrylate-PSA tape with Rayon backing (from Example 2) and the hot-melt Acrylate-PSA tape with Rayon backing (from Comparative Example 2) were applied to a subject's bare-skin back. Nine hot-melt PSA tape samples were sequentially applied to Test Site A, each rolled down with a 2.3-kg roller four times (two cycles), and each removed immediately. Similarly, nine BMF-PSA tape samples were applied, rolled, and removed from Test Site B. The cumulative amounts of keratin removed from Test Sites A and B were then determined according to the Keratin Assay Method described in the Test Protocols. Evaluation results are shown graphically in FIG. 2. As is clearly evident from the data, a significantly greater amount of keratin was removed from Test Site A (hot-melt Acrylate-PSA Tape Site), thereby reflecting greater trauma, than was removed from Test Site B (BMF-Acrylate-PSA Tape Site).

Example 4

BMF-KRATON™-PSA Web

A tackified block copolymer based BMF-PSA web was prepared as was adhesive 2 except the primary air was maintained at 180° C. and 241 KPa with a 0.076 cm gap width to produce a uniform web. The feedblock assembly was fed by a polymer melt stream (180° C.) comprised of a precompounded mixture of KRATON™ 1112 (100 parts, a styrene/isoprene/styrene block copolymer available from Shell Chemical, Houston, Tex.), ESCOREZ 1310 LC (80 parts, an aliphatic hydrocarbon tackifier available from Exxon Chemical Co., Houston, Tex.) and ZONAREZ-A25 (10 parts, an alpha pinene type resin available from Arizona Chemical, Panama City, Fla.) and delivered to one of the gear pumps at 180° C. The BMF-PSA web was collected on a double coated silicone release paper (Daubert Coated Products, Westchester, Ill.) which passed around a rotating drum collector at a collector to die distance of 17.8 cm. The resulting BMF-PSA web, comprising PSA microfibers having an average diameter of less than 25 microns as determined using the Scanning Electron Microscope had a basis weight of about 51 g/m$^2$.

Examples 5 and 6

BMF-KRATON™-PSA Web and Crimped Fibers

Composite fibrous webs were prepared on apparatus as described in U.S. Pat. No. 4,118,531 (Hauser), which is incorporated herein by reference, using the BMF-KRATON™ PSA microfibers of Example 4 less than 25 microns in diameter and 6 denier, 3.8 cm long, 10 crimps per 2.54 cm polyester staple fibers (Type 295 TREVIRA™ polyester available from Hoechst Fibers Industries, Spartanburg, S.C.). Two webs were prepared including 5 percent staple fiber (Example 5) and 10 percent staple fiber (Example 6) by weight, with the balance in each case being blown microfibers.

Comparison Example 4

Cast Adhesive

A double coated tape using a 1 mil polyester film with a KRATON™ cast pressure-sensitive adhesive (available as 3M 9877 from 3M, St. Paul, Minn.) was used.

Moisture Vapor Transmission Rate (MVTR)

Moisture vapor transmission rates (MVTR) were measured using a modification of ASTM-E96-80 Upright Water Method, low humidity on one side and high humidity on the other. The modification was made to measure the MVTR through the cross sectional area of the adhesive. Water (approximately 10 eyedroppers full) was placed in a cup with a 10 mm land. A 0.0254 mm (2 mil) polyester film was laminated to the webs from Example 1, Example 2, Example 3. Comparison Example 4 was laminated on one side to the 0.0254 mm polyester film. Circles 6.35 cm (2 ½ inch) in diameter were cut from the laminated film and placed over the top of the cup and the land. These assemblies were weighed and placed in a test chamber. The test chamber conditions were 40.1° C. and 20.6 percent relative humidity. The assemblies were reweighed at four consecutive 24 hour intervals. Results are shown in Table 1 and are reported in $g/m^2/24$ hr.

TABLE 1

MVTR for Adhesive Cross Sectional Area

| Example | 1–24 hour Interval ($gm/m^2/24$ hours) | | 2–24 hour Interval ($gm/m^2/24$ hours) | | 3–24 hour Interval ($gm/m^2/24$ hours) | | 4–24 hour Interval ($gm/m^2/24$ hours) | |
|---|---|---|---|---|---|---|---|---|
| | Average | Std Dev. | Average | Std. Dev. | Average | Std. Dev. | Average | Std. Dev. |
| 4 | 6296 | 0 | 5037 | 0 | 3148 | 890 | 3777 | 1781 |
| 5 | 14365 | 4617 | 12080 | 4155 | 12406 | 1847 | 13059 | 2770 |
| 6 | 38524 | 36013 | 11100 | 923 | 12733 | 2309 | 12080 | 1385 |
| Comp. 4 | 2644 | 1247 | 1763 | 0 | 1763 | 0 | 0 | 0 |

The fibrous adhesives of Example 5 and Example 6 improve the moisture vapor transmission rate by 200–300 percent due to increased porosity.

Examples 7–9

Tape

The webs from Example 4, Example 5, and Example 6 are laminated to a nonwoven spunlaced polyester, fabric (available as SONTARA™ from E. I. Du Pont de Nemours & Co., Old Hickory, Tenn.) forming tapes. Optionally the webs could be laminated to a film with capillaries therein (available as VISPORE™ polymer fabrics [40 hex LDPE] from Tredegar Industries Inc., Richmond, Va.

Example 10–12

Nasal Dilator

Resilient members made from 3M 9952 tape, 0.254 mm (10 mil) polyester single coated with an acrylic adhesive are secured to one side of the tapes of Examples 7–9. The resilient members can optionally be covered with a flexible strip of top material, such as 3M 1533 tape, 0.127 mm (5 mil) tan micropore rayon nonwoven adhesive coated on one side with a breathable, acrylic pressure-sensitive adhesive. The strip of top material covers and is secured to the resilient members and to one side of the nonwoven spunlaced polyester fabric.

I claim:

1. A nasal dilator comprising a backing substrate having a first face and a second face, the first facing provided with a fibrous adhesive layer comprising an entangled web of pressure-sensitive adhesive fibers which web has a moisture vapor transmission rate (MVTR, as defined in the Examples) of at least 1000 $g/m^2$/day after one day, an initial adhesion to skin of at least 20 g/2.5 cm, the backing substrate second face having a resilient spring extending along the length direction of the backing substrate and adhered to the backing substrate at/at least two end regions thereof.

2. The nasal dilator of claim 1 wherein the backing substrate has two end regions and an intermediate section where the resilient spring is attached to the end regions and not the intermediate section.

3. The nasal dilator of claim 2 wherein the backing substrate is a nonwoven web.

4. The nasal dilator of claim 2 wherein the basis weight of the fibrous adhesive layer is from 20 to 100 $g/m^2$.

5. The nasal dilator of claim 1 wherein the resilient spring comprises one or more resilient spring elements.

6. The nasal dilator of claim 5 wherein the resilient spring comprises two or more resilient spring elements.

7. The nasal dilator of claim 5 wherein the resilient spring provides a recovery force when bent around a nose of from 5 to 50 grams force.

8. The nasal dilator of claim 7 wherein the resilient spring provides a recovery force when bent around a nose of from 20 to 30 grams force.

9. The nasal dilator of claim 5 wherein the resilient spring elements comprise a thermoplastic film stay having a thickness of from 200 to 375 microns.

10. The nasal dilator of claim 5 wherein the resilient spring elements extend to within 500 microns or less of first and second ends of the backing substrate.

11. The nasal dilator of claim 5 further comprising a top facing layer.

12. The nasal dilator of claim 11 wherein the top facing layer is coextensive with the backing layer.

13. The nasal dilator of claim 5 wherein the top facing layer covers at least the resilient spring elements.

14. The nasal dilator of claim 1 wherein the backing substrate is breathable.

15. The nasal dilator of claim 1 wherein the basis weight of the fibrous adhesive layer is from 5 to 200 $g/m^2$.

16. The nasal dilator of claim 1 wherein the adhesive coated substrate has a peel to skin of from 30 to 70 g/2.5 cm.

17. The nasal dilator of claim 1 wherein the adhesive layer comprises commingled pressure-sensitive adhesive fibers and 2 to 20 percent by weight non-pressure-sensitive adhesive fibers.

18. The nasal dilator of claim 1 wherein the pressure-sensitive adhesive fibers comprise a blend of a pressure-sensitive adhesive phase and a thermoplastic phase.

19. The nasal dilator of claim 1 wherein the pressure-sensitive adhesive fibers have two or more layers along the length of the fibers at least one layer being a pressure-sensitive adhesive layer forming at least a portion of the outer surface of the fiber and at least one second layer of a thermoplastic material.

20. The nasal dilator of claim 19 wherein the layers are side by side.

21. The nasal dilator of claim 1 wherein the pressure-sensitive adhesive fibers have an average diameter of less than about 100 microns.

22. The nasal dilator of claim 1 wherein the pressure-sensitive adhesive fibers are formed from a tackified rubber-resin adhesive.

23. The nasal dilator of claim 22 wherein the tackified rubber-resin adhesive comprises an A-B type block copolymer and a compatible resin.

24. The nasal dilator of claim 1 wherein the pressure-sensitive adhesive fiber comprises a polyalphaolefin adhesive.

25. The nasal dilator of claim 1 wherein the pressure-sensitive adhesive fibers comprises an acrylate pressure-sensitive adhesive.

26. The nasal dilator of claim 1 wherein the breathable adhesive layer is coated over the entire first face of the backing substrate.

27. The nasal dilator of claim 1 wherein only the first and second end regions of the backing substrate first face are provided with the fibrous adhesive layer.

28. The nasal dilator of claim 1 wherein the breathable adhesive layer has a MVTR of at least 3000 $g/m^2/day$.

29. The nasal dilator of claim 1 wherein the breathable adhesive layer has a MVTR of at least 10,000 $g/m^2/day$.

30. A nasal dilator comprising a backing substrate having a first face and a second face, the first face being provided with a fibrous breathable adhesive layer comprising an entangled web of pressure-sensitive adhesive fibers, which web has a moisture vapor transmission rate (MVTR) of at least 1000 $grams/m^2/day$ after one day (as defined in the Examples), and an adhesion to skin of at least 20 grams/2.5 cm, the backing substrate comprising a resilient spring providing a recovery force when bent around the nose of from 5 to 50 grams force.

31. The nasal dilator of claim 30 wherein the breathable adhesive layer has a MVTR of at least 3000 $g/m^2/day$.

32. The nasal dilator of claim 30 wherein the breathable adhesive layer has a MVTR of at least 10,000 $g/m^2/day$.

* * * * *

UNITED STATES PATENT AND TRADEMARK OFFICE
CERTIFICATE OF CORRECTION

PATENT NO.    : 5,957,126
DATED         : September 28, 1999
INVENTOR(S)   : Roger Dwayne Neeser It is certified that error appears in the above-identified patent and that said Letters Patent is hereby corrected as shown below:

Column 8,
Line 63, please delete "mnicrofibers" and insert -- microfibers --.

Signed and Sealed this

Second Day of April, 2002

Attest:

JAMES E. ROGAN
*Attesting Officer*   *Director of the United States Patent and Trademark Office*